(12) United States Patent
Barnhizer et al.

(10) Patent No.: US 9,068,216 B2
(45) Date of Patent: *Jun. 30, 2015

(54) METHODS AND DEVICES FOR RAPID DETECTION AND IDENTIFICATION OF LIVE MICROORGANISMS BY APTAMERS AND/OR ANTIBODIES IMMOBILIZED ON PERMEABLE MEMBRANES

(76) Inventors: Bret T. Barnhizer, Hubbard, OH (US); Sergey Gazenko, Mason, OH (US)

( * ) Notice: Subject to any disclaimer, the term of this patent is extended or adjusted under 35 U.S.C. 154(b) by 235 days.

This patent is subject to a terminal disclaimer.

(21) Appl. No.: 13/350,127

(22) Filed: Jan. 13, 2012
(Under 37 CFR 1.47)

(65) Prior Publication Data
US 2012/0129157 A1 May 24, 2012

(51) Int. Cl.
*C12Q 1/04* (2006.01)
*C12Q 1/06* (2006.01)

(52) U.S. Cl.
CPC ... *C12Q 1/04* (2013.01); *C12Q 1/06* (2013.01)

(58) Field of Classification Search
None
See application file for complete search history.

(56) References Cited

U.S. PATENT DOCUMENTS

| | | | |
|---|---|---|---|
| 4,237,223 A | | 12/1980 | Metz |
| 5,100,801 A | * | 3/1992 | Ward et al. ............... 435/304.2 |
| 5,624,815 A | | 4/1997 | Grant et al. |
| 5,650,323 A | | 7/1997 | Root |
| 5,660,990 A | | 8/1997 | Rao et al. |
| 5,716,798 A | | 2/1998 | Monthony et al. |
| 5,770,440 A | | 6/1998 | Berndt |
| 6,015,681 A | * | 1/2000 | Ralls et al. ................ 435/7.32 |
| 6,146,836 A | * | 11/2000 | Barlow ....................... 435/7.1 |
| 6,372,183 B1 | | 4/2002 | Akong et al. |
| 6,503,702 B1 | | 1/2003 | Stewart |
| 6,696,286 B1 | | 2/2004 | Halverson et al. |
| 6,729,352 B2 | | 5/2004 | O'Connor et al. |
| 6,743,581 B1 | | 6/2004 | Vo-Dinh |
| 6,767,706 B2 | | 7/2004 | Quake et al. |
| 6,818,435 B2 | | 11/2004 | Carhalho et al. |
| 6,852,222 B2 | | 2/2005 | Clark et al. |
| 8,133,720 B2 | * | 3/2012 | Ono et al. ................ 435/287.2 |
| 2002/0189374 A1 | | 12/2002 | DeSilets et al. |
| 2005/0009113 A1 | | 1/2005 | Goldbard et al. |
| 2005/0026135 A1 | * | 2/2005 | Gazenko ......................... 435/4 |
| 2006/0088895 A1 | | 4/2006 | Wanders et al. |

FOREIGN PATENT DOCUMENTS

WO    WO 2007/084886    *   7/2007

OTHER PUBLICATIONS

Song et al. Aptamer-based biosensors. Trends in Analytical Chemistry, vol. 27, No. 2, p. 108-117, 2008.*
Pierce DAB substrate kit info downloaded from http://www.piercenet.com/browse.cfm?fldID=01041015 on Sep. 18, 2013.*
Faro, J. et al., Rapid Diagnostic Test for Identifying Group B *Streptococcus*. Am. J. Perinatology, Aug. 2011, pp. 811-814, vol. 28.
Moorthy et al., In Situ Fabricated Porous Filters for Microsystems, Lab Chip, Apr. 2003, pp. 62-66, vol. 3.
Ingram, D.T. et al., Development of a Colony Lift Immunoassay to Facilitate Rapid Detection and Quantification of *Escherichia coli* O157:H7 from Agar Plates and Filter Monitor Membranes; Clinical and Diagnostic Laboratory Immunology, Jul. 1998, pp. 567-573, vol. 5, No. 4.
Rice, B.E. et al., Development of a Rapid and Specific Colony-Lift Immunoassay for Detection and Enumeration of *Campylobacter jejuni, C. coli*, and *C. lari*; Clinical and Diagnostic Laboratory Immunology, Nov. 1996, pp. 669-677, vol. 3, No. 6.
Tse et al., Membrane Filter Staining Method: Bacterial Plate Counts in 24 H, Applied and Environmental Microbiology, 1984, pp. 433-434, vol. 48, No. 2.
Mattman et al., Cellophane Membranes in Growth of L. Variants of the Genus *Proteus*, Applied Microbiology, Mar. 1984, pp. 153-154, vol. 6, No. 2.

* cited by examiner

*Primary Examiner* — Oluwatosin Ogunbiyi
(74) *Attorney, Agent, or Firm* — Acker Wood IP Law, LL; Gwen R. Acker Wood

(57) ABSTRACT

The invention provides methods, devices and kits for rapid detection and identification of one or more live target microorganisms in a liquid sample or grown on plates containing nutrient media. The invention includes mixing one or more target microorganisms with one or more aptamers and/or one or more antibodies, each conjugated to a reporter compound and specific for a first site on or more target microorganisms to form a mixture. The mixture is placed on a permeable membrane having immobilized thereon one or more aptamers linked to an amine compound, and/or one or more antibodies, each specific for a second site on one or more target microorganisms or a site on the aptamer conjugate and/or antibody conjugate. A detection solution is added to the membrane and detection and identification of one or more target microorganisms is achieved in about one hour or less.

14 Claims, 8 Drawing Sheets

METHODS AND DEVICES FOR RAPID DETECTION AND IDENTIFICATION OF LIVE MICROORGANISMS BY APTAMERS AND/OR ANTIBODIES IMMOBILIZED ON PERMEABLE MEMBRANES

CROSS REFERENCE TO RELATED APPLICATIONS

This application is a continuation-in-part of U.S. application Ser. No. 13/346,939, filed Jan. 10, 2012, abandoned, which is a continuation-in-part of Ser. No. 12/785,180, filed May 21, 2010, abandoned, which is a continuation-in-part of U.S. application Ser. No. 12/532,501, filed Mar. 16, 2010, which is a Section 371 of PCT/U.S. Ser. No. 08/003,826, filed Mar. 24, 2008, which claims priority to U.S. Provisional Application No. 60/896,321, filed Mar. 22, 2007, all of which are incorporated herein by reference.

FIELD OF THE INVENTION

The present invention relates generally to the field of microbiology and, in particular, to microbiological diagnostics for the rapid detection and identification of target microorganisms.

BACKGROUND OF THE INVENTION

Modern microbiological diagnostic assays employ two different growth protocols for analysis, i.e., detection, identification and/or enumeration, of microorganisms: (1) analysis without preliminary growth of the microorganisms or (2) analysis after preliminary growth of microorganisms. Analysis of microorganisms without preliminary growth includes the use of methods such as: (1) immunological analyses, e.g., immunofluorescence, radioimmunoassay, enzyme immunoassay (EIA) for single cells and others; (2) DNA/RNA analyses via polymerase chain reaction (PCR); and (3) flow cytometry (FC) analyses (detection of single cells after labeling with fluorescent antibodies or fluorogenic substrates). Artificial substrates may also be used for detection and analysis of microorganisms by microscopic means. Microbiological diagnostic assays that analyze microorganisms after preliminary growth of the microorganisms include enzyme-linked immunosorbent assay (ELISA), mass-spectrometry, Fourier transform infrared (FTIR) spectroscopy, immune analyses and others.

Whether one chooses to use diagnostic assays with or without preliminary growth of microorganisms, all of the current diagnostic assays are cost, time and labor intensive and require the use of sophisticated laboratory equipment and personnel.

Along with the above-described sophisticated techniques, the traditional method of colony growth on a Petri plate still is the most common method used to detect live microorganisms in a sample. However, analysis by Petri plate also can be time and labor intensive. In order to create colonies, inoculated plates typically are incubated approximately 24 to 48 hours for bacteria and 72 to 120 hours for fungi. Thus, a relatively long time is needed to form colonies easily visible to the naked eye. If the sample arises from a time-sensitive biohazard incident, a hospital patient in critical condition, or industrial (food, pharmaceutical) products having a short shelf life, then time is of the essence and time-consuming incubation and serial testing can be a substantial burden with potentially life-threatening or profit loss consequences. Colonies appearing on solid nutrient media typically are counted for detection and enumeration of total microbial growth or are removed and analyzed according to traditional microbiological procedures, e.g., mass-spectrometry, Fourier transform infrared spectroscopy (FTIR) spectroscopy, chromatography, immunoassays or PCR.

In the field of medicine, in the food, biotechnological and pharmaceutical industries, for military and civilian defense, and environmental control, it is very important to have rapid, simple and reliable identification of colonies and microcolonies. For example, pathogens which affect the food industry are *E. coli, Salmonella* spp., *Listeria* spp., *Pseudomonas aeruginosa, Staphylococcus aureus*, some *Lactobacillus* spp., *Bacillus cereus*, some yeast and molds and other microorganisms. Pathogens which require rapid identification for military and civilian defense include, for example, anthrax, where time is of the essence. Reliable monoclonal and polyclonal antibodies exist for a majority of these organisms but they are most useful only after a high quantity of cells are grown on a special media or broth and then identified by EIA or ELISA using sophisticated and expensive equipment such as VITEC™ (bioMerieux) by fluorescence or using 96-well plates with specific antibodies immobilized inside the wells.

Consequently, there is a need for a rapid, accurate and cost-effective method to selectively detect and identify live microorganisms which overcomes the limitations of the prior art.

SUMMARY OF THE INVENTION

The present invention fulfills this need by providing methods and devices for rapid detection and identification of live target microorganisms contained in a liquid sample or after a short growth time of a sample on nutrient media. The detection and identification of target microorganisms may be achieved in as little as one hour or less, a very short time period not previously encountered with other diagnostic assays known to date.

In one aspect of the invention, there is provided a method for rapid detection and identification of one or more live target microorganisms in a sample, the method comprising the steps of obtaining a sample containing at least one target microorganism; forming a mixture containing the at least one microcolony from the at least one target microorganism and at least one first aptamer conjugated to a reporter compound and selected for a binding site of the at least one target microorganism and/or of at least one first antibody conjugated to a reporter compound and specific for an antigenic site of the at least one target microorganism; washing the mixture; adding the mixture to a permeable membrane, the permeable membrane having immobilized thereon at least one second aptamer selected for a binding site of the at least one first aptamer and/or at least one second antibody specific for an antigenic site of the at least one first antibody; washing any non-bound microorganisms from the permeable membrane; and adding a detection solution to the permeable membrane in order to detect and identify the at least one target microorganism, wherein the detection and identification of the at least one microorganism is achieved in one hour or less.

In an embodiment, the sample is a liquid sample containing at least one or more live target microorganisms.

In another embodiment, the sample is obtained by placing a sample containing at least one target microorganism on a nutrient medium and incubating the sample for a period of time in order to grow at least one microcolony from the at least one target microorganism.

In another aspect of the invention, there is provided a method for rapid detection and identification of one or more live target microorganisms in a sample, comprising the steps of obtaining a sample containing at least one target microorganism; forming a mixture containing the at least one microcolony from the at least one target microorganism and at least one first aptamer conjugated to a reporter compound and selected for a first binding site of the at least one target microorganism and/or at least one first antibody conjugated to a reporter compound and specific for a first antigenic site of the at least one target microorganism; adding the mixture to a permeable membrane having immobilized thereon at least one second aptamer selected for a second binding site of the at least one target microorganism and/or at least one second antibody specific for a second antigenic site of the at least one target microorganism; washing any non-bound microorganisms from the permeable membrane; and adding a detection solution to the permeable membrane in order to detect and identify the at least one target microorganism, wherein the detection and identification of the at least one microorganism is achieved in one hour or less.

In an embodiment, the sample is a liquid sample containing at least one or more live target microorganisms.

In another embodiment, the sample is placed on a nutrient medium and incubated for a period of time in order to grow at least one microcolony from the at least one target microorganism.

In another aspect of the invention, there is provided a device for rapid detection and identification of one or more live target microorganisms in a sample, the device comprising a container having therein nutrient medium to grow at least one microcolony from at least one live target microorganism; at least one first aptamer conjugated to a reporter compound and selected against a binding site of the at least one target microorganism and/or at least one first antibody conjugated to a reporter compound and specific for an antigenic site of the at least one target microorganism; a permeable membrane having immobilized thereon at least one second aptamer selected against a binding site of the at least one first aptamer and/or at least one second antibody specific for an antigenic site of the at least one first antibody; a portable washing apparatus; and a detection solution for detecting and identifying the at least one target microorganism bound on the permeable membrane in one hour or less.

In another aspect of the invention, there is provided a device for rapid detection and identification of one or more live target microorganisms in a sample, the device comprising a container having therein nutrient medium to grow at least one microcolony from at least one live target microorganism; at least one first aptamer conjugated to a reporter compound and selected against a first binding site of the at least one target microorganism and/or at least one first antibody conjugated to a reporter compound and specific for a first antigenic site of the at least one target microorganism; a permeable membrane having immobilized thereon at least one second aptamer selected against a second binding site of the at least one target microorganism and/or at least one second antibody specific for a second antigenic site of the at least one target microorganism; a portable washing apparatus; and a detection solution for detecting and identifying the at least one target microorganism bound on the permeable membrane in one hour or less.

The invention also includes test kits comprised of the methods and devices described hereinabove.

The at least one second aptamer of the invention may be linked to an amine compound, which includes without limitation, bovine serum albumin, amine linkers and other compounds which contain an amine group.

The at least one type of antibody includes, without limitation, a monoclonal or a polyclonal antibody.

Target microorganisms that can be detected and identified according to the embodiments of the present invention include, without limitation, bacteria, yeasts, fungi, viruses, cells and eukaryotic cells.

Suitable nutrient media contemplated for growing the at least one microorganism in a sample include, without limitation, agar such as tryptic soy agar or sheep blood agar.

Suitable permeable membranes contemplated for use in the present invention include, without limitation, polymers such as nitrocellulose, regenerated cellulose and its derivatives such as cellophane, cuprophane and dialysis membranes, nylon or polyvinylidene fluoride (PVDF) and other polymers such as organic or inorganic materials with naturally occurring pores or artificially created pores.

Suitable reporter compounds contemplated for use in the present invention include, without limitation, chromogenic substrates such as tetrazolium dyes such as MTT [3-(4,5-dimethylthiazol-2-yl)-2,5-diphenyltetrazolium bromide], INT [2-(p-iodophenyl-3-(p-nitrophenyl tetrazolium chloride], resazurine and other chromogenic substrates; fluorogenic substrates such as fluorescein isothiocyanate (FITC); and enzymes such as horse-radish peroxidase.

Suitable detection solutions contemplated for use in the present invention include, without limitation, enzymes such as alkaline phosphatase and staining solutions such as 3,3'-diaminobenzidine (DAB).

Portable washing apparatuses are well known in the art, any of which may be used in the methods and devices of the invention.

The methods and devices of the invention allow for rapid detection and identification of target microorganisms in one hour or less. In an embodiment, target microorganisms of the invention are detected and identified in 30 minutes or less.

BRIEF DESCRIPTION OF THE DRAWINGS

The drawings included herewith are incorporated in and form a part of this specification. The drawings illustrate embodiments of the present disclosure and, together with the description, serve to explain the principles of the disclosure. It should be understood that the drawings referred to in this description are not drawn to scale unless specifically noted as such.

DETAILED DESCRIPTION OF THE INVENTION

Figure 1:
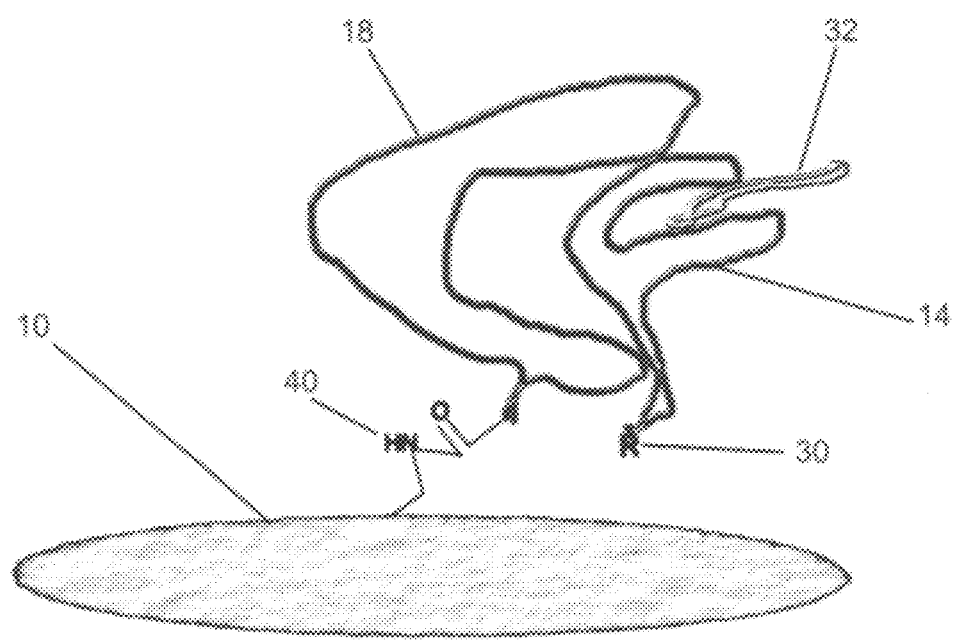
FIG. 1 shows an aptamer (referred to herein as a first aptamer) bound by another aptamer (referred to herein as a second aptamer). The first aptamer is conjugated to a reporter compound and is bound to a target microorganism. The second aptamer is immobilized on a permeable membrane via linkage to an amine compound.

The present invention provides methods and devices for detecting and identifying live microorganisms which are extremely rapid and which do not require sophisticated laboratory equipment such as flow cytometers, mass-spectrometers, FTIR spectroscopy or PCR.

The present invention is based on the ability of live target microorganisms to bind selectively and with high specificity to unbound aptamers and/or antibodies and to aptamers and/or antibodies immobilized on permeable membranes.

The present invention allows for the detection and identification of many different types of microorganisms, such as bacteria, yeasts, fungi, spores, eukaryotic cells, cells, viruses or proteins.

Aptamers, nucleic acid sequences having unique properties, were first identified from very large random sequence oligonucleotide libraries in 1990 by Tuerk C. et al. (Science, 1990, 249:505-10) and Ellington, A. D. et al. (Nature, 1990; 346:818-22), both papers incorporated herein by reference. The selection method for aptamers, called the SELEX (systemic evolution of ligands by exponential enrichment) process, is a technique which screens very large combinatorial libraries of oligonucleotides by an iterative process of in vitro selection and amplification. Combinatorial libraries based on replicable biopolymers such as nucleic acids (and peptides) offer the convenience of iterative amplification of their members, making the screening process fast and easy.

The screening process, a random sequence oligonucleotide library is incubated with a target of interest. During this step, a very small fraction of individual sequences tends to interact with the target, and these sequences are separated from the rest of the library by means of any one of several physical separation techniques known in the art. Typically, nitrocellulose filter partitioning is used with protein targets that are retained on nitrocellulose. Small molecular targets are generally immobilized on a solid support to generate an affinity matrix, in which case sequences that do not interact with the target on the solid support can be removed easily by a simple washing step. The population of sequences bound to the target is isolated and amplified to obtain an enriched library to be used for the next selection/amplification cycle. The enrichment efficiency of high-affinity binders is governed by the stringency of selection at each round. The progress of the enrichment of high-affinity binders can be determined by carrying out binding analysis of enriching populations against the target. Once affinity saturation is achieved after several rounds of selection/amplification, the enriched library is cloned and sequenced to obtain the sequence information of each member. Individual sequences are further characterized on the basis of their ability to bind to the target. The majority of individual sequences, greater than 90%, in an enriched library are aptamers that bind successfully to the target used for selection.

Aptamers have the capacity to recognize virtually any class of target compounds with high affinity and specificity which rival antibodies in both therapeutic and diagnostic applications. Aptamers are much smaller and less complex than antibodies, and thus are easier to manufacture and modify. Aptamers mimic properties of antibodies in a variety of diagnostic formats, but are very different from antibodies, having characteristics that overcome many shortcomings of antibodies when used in diagnostic applications. Some of the shortcomings of antibodies include difficulty in growing high yields of monoclonal antibodies in vivo, as they typically are grown as hybridomas in peritoneal cavities of animals and purified from ascites fluid; performance of the same antibody tends to vary from batch to batch, requiring immunoassays to be re-optimized with each new batch of antibodies; identification of antibodies that could recognize targets under conditions other than physiological conditions is not feasible; kinetic parameters of antibody-target interactions cannot be changed on demand; antibodies are sensitive to temperature and undergo irreversible denaturation; and antibodies have a limited shelf life.

In contrast, aptamers possess many advantages when used in diagnostic applications. First, aptamers exhibit extraordinary specificity. For example, the aptamer selected against theophylline, a purine derivative used to treat asthma, binds with a 10,000-fold lower affinity to caffeine, another purine analog, which differs from theophylline by only one methyl group. Second, aptamers can be identified through an in vitro process that does not depend on animals, cells, or in vivo conditions. As a result, the properties of aptamers can be modified on demand. Third, selection conditions can be manipulated to obtain aptamers with properties desirable for in vitro diagnostics. For example, aptamers that bind to a target in a non-physiological buffer and at non-physiological temperatures can be identified. Similarly, kinetic parameters, such as the on- and off-rates of aptamers, can be changed on demand. Fourth, because animals or cells are not involved in aptamer identification, toxins as well as compounds which do not elicit good immune responses can be used to generate high-affinity aptamers. Fifth, aptamers are produced by chemical synthesis with extreme accuracy and reproducibility. They are purified under denaturing conditions to a very high degree of purity. Therefore, little or no batch-to-batch variation is encountered in aptamer production. Sixth, reporter compounds such as biotin, HRP and fluorescein can be attached to aptamers at precise locations identified by the user. Functional groups that allow subsequent derivatization of aptamers with other compounds can also be attached during chemical synthesis of aptamers. Seventh, although aptamers undergo denaturation, the process is reversible. After being denatured, functional aptamers can be regenerated easily within minutes. Eighth, aptamers are stable to long-term storage and can be transported at ambient temperature, and thus can tolerate transportation without special requirements for cooling, eliminating the need for a continuous cold chain.

The present invention takes advantage of the superior qualities and unique characteristics of aptamers in concert with antibody technology to arrive at extremely rapid assays to detect and identify target microorganisms in as little one hour or less and, in most cases, 30 minutes or less.

The permeable membranes encompassed by the present invention include, without limitation, polymers such as nitrocellulose, regenerated cellulose and its derivatives such as cellophane, cuprophane and dialysis membranes, nylon or polyvinylidene fluoride (PVDF) and other polymers such as organic or inorganic materials with naturally occurring pores or artificially created pores. In particular, nitrocellulose membranes are able to bind amine ($NH_2$)-containing compounds on their surfaces because of the strong interaction of nitrite ($NO_2$) groups contained in the nitrocellulose membrane with the $NH_2$ groups contained in the compounds. The aptamer compounds encompassed by the present invention are linked to $NH_2$-containing compounds which include, without limitation, amine linkers, biotin, bovine serum albumin (BSA) compounds or other $NH_2$-containing compounds, and thus are easily immobilized on the permeable membranes of the present invention. The $NH_2$-containing compounds are linked to the 5'-end of the aptamer compounds during oligonucleotide synthesis, according to synthetic protocols known by those in the art. All antibody compounds contain $NH_2$ groups, and thus the antibodies encompassed by the present invention also are easily immobilized on permeable membranes. Monoclonal antibodies, polyclonal antibodies or a combination of both may be used in the methods of the present invention. Lectins or other natural agglutinins also may be used in place of antibodies. Whether the permeable membrane of the invention has immobilized aptamers and/or antibodies on its surface, spaces in the permeable membrane not filled with the aptamers and/or antibodies are filled with a blocking buffer compound, such as milk powder, BSA, biotin or other proteinaceous compounds, so that all spaces of the permeable membrane are filled.

The following figures show the various configurations in which aptamers and/or antibodies may be employed in the methods of the invention to allow for the extraordinary and surprisingly rapid detection and identification of target microorganisms.

Referring to FIG. 1, a permeable membrane 10 is shown with an aptamer 18 (referred to herein as a second aptamer) immobilized thereon. The second aptamer 18 is linked to an amine compound 40 which immobilizes the second aptamer 18 to the permeable membrane 10. The second aptamer 18 is bound to a different aptamer 14 (referred to herein as a first aptamer), which is bound to a target microorganism 32. The first aptamer 14 is conjugated to a reporter compound 30 which includes, without limitation, chromogenic substrates such as tetrazolium dyes such as MTT [3-(4,5-dimethylthiazol-2-yl)-2,5-diphenyltetrazolium bromide], INT [2-(p-iodophenyl-3-(p-nitrophenyl tetrazolium chloride], resazurine and other chromogenic substrates; fluorogenic substrates such as fluorescein isothiocyanate (FITC); or enzymes such as horse-radish peroxidase. After the permeable membrane 10 is washed, a detection solution, which includes, without limitation, 3,3'-diaminobenzidine (DAB) or alkaline phosphatase, is added to the permeable membrane 10 which changes the color of the permeable membrane 10 in locations where the target microorganism 32 is attached to the permeable membrane 10 via binding to the immobilized second aptamer 18.

Figure 2:
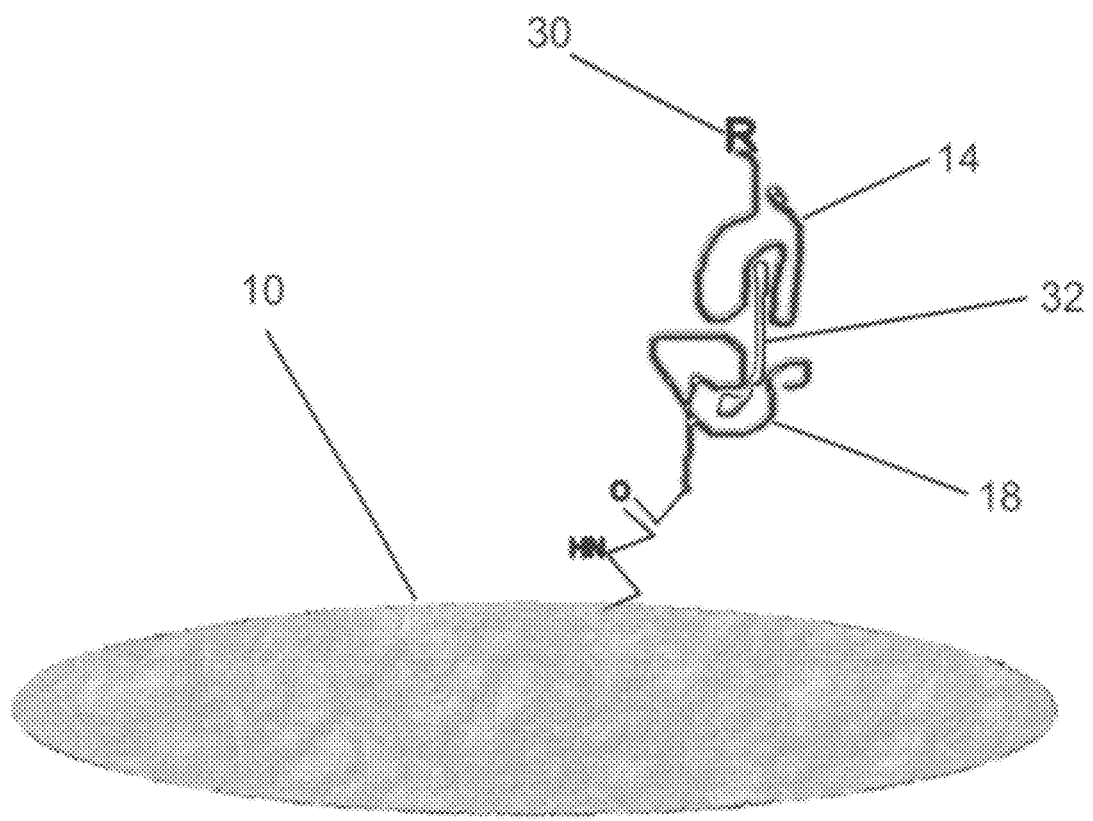
FIG. 2 shows an aptamer (referred to herein as a first aptamer) bound to one site of a target microorganism, the first aptamer conjugated to a reporter compound, and a permeable membrane having an immobilized aptamer thereon (referred to herein as a second aptamer) bound to a second site of the target microorganism. The second aptamer is linked to an amine compound which immobilizes the second aptamer to the permeable membrane.

Referring to FIG. 2, a permeable membrane 10 is shown with an aptamer 18 (referred to herein as a second aptamer) immobilized thereon. The second aptamer 18 is linked to an amine compound which immobilizes the second aptamer 18 to the permeable membrane 10. The second aptamer 18 is bound to one site of a target microorganism 32 and a different aptamer 14 (referred to herein as a first aptamer) is bound to a different site of the target microorganism 32. The first aptamer 14 is conjugated to a reporter compound 30 as described above. After the permeable membrane 10 is washed, a detection solution, as described above, is added to the permeable membrane 10 which changes the color of the permeable membrane 10 in locations where the target microorganism 32 is attached to the permeable membrane 10 via binding to the immobilized second aptamer 18.

Figure 3:
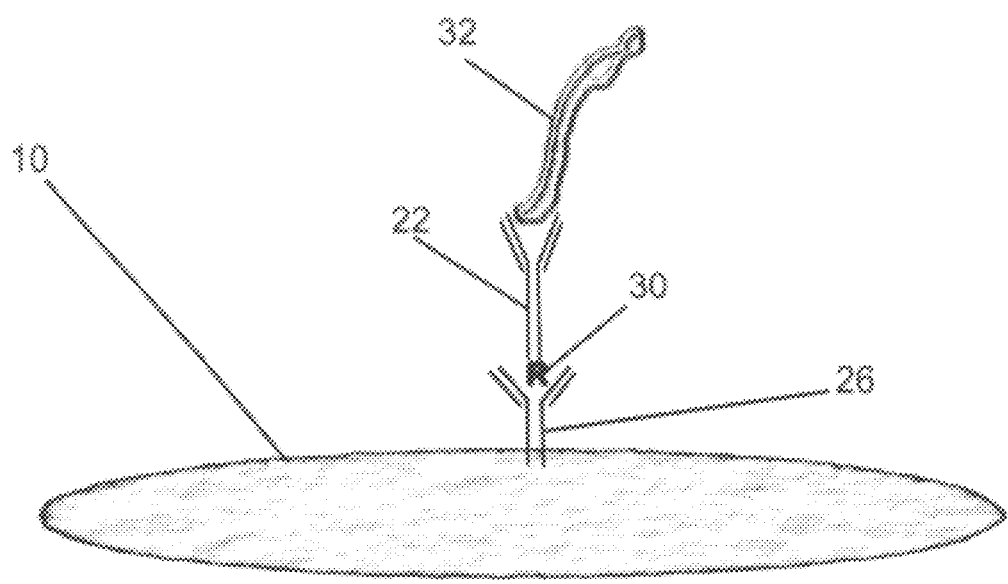
FIG. 3 shows an antibody (referred to herein as a first antibody) bound by another antibody (referred to herein as a second antibody). The first antibody is conjugated to a reporter compound and is bound to a target microorganism. The second antibody is immobilized on a permeable membrane.

Referring to FIG. 3, a permeable membrane 10 is shown with an antibody 26 (referred to herein as a second antibody) immobilized thereon. The second antibody 26 is bound to a different antibody 22 (referred to herein as a first antibody), which is bound to a target microorganism 32. The first antibody 22 is conjugated to a reporter compound 30 as described above. After the permeable membrane 10 is washed, a detection solution, as described above, is added to the permeable membrane 10 which changes the color of the permeable membrane 10 in locations where the target microorganism 32 is attached to the permeable membrane 10 via binding to the immobilized second antibody 26.

Figure 4:
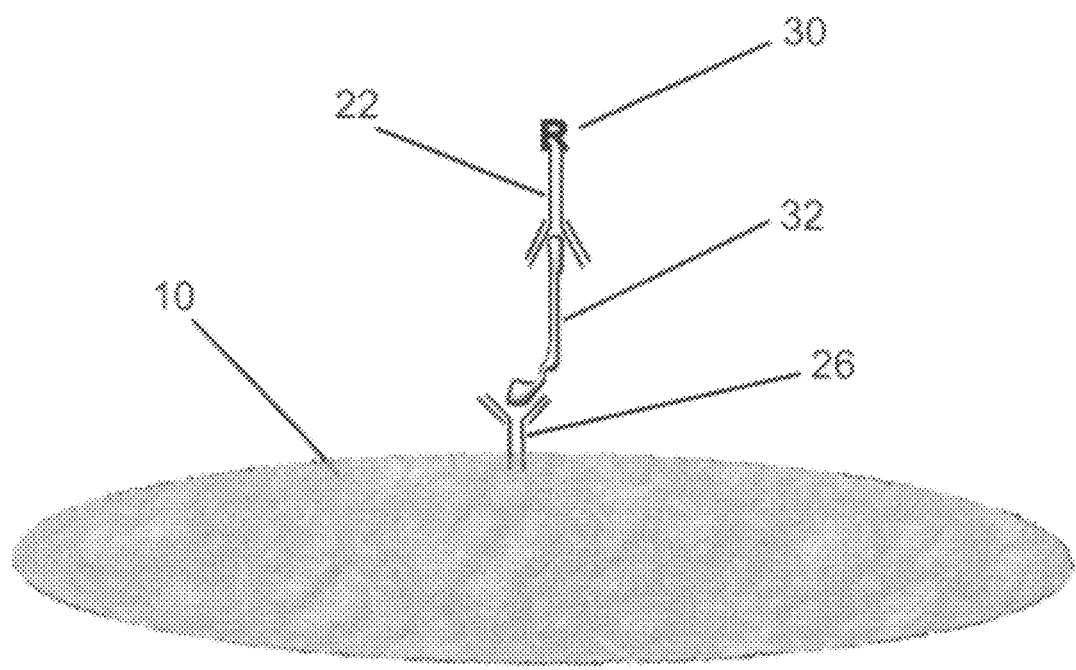
FIG. 4 shows an antibody (referred to herein as a first antibody) bound to one site of a target microorganism, the first antibody conjugated to a reporter compound, and a permeable membrane having an immobilized antibody thereon (referred to herein as a second antibody), the second antibody bound to a second site of the target microorganism.

Referring to FIG. 4, a permeable membrane 10 is shown with an antibody 26 (referred to herein as a second antibody) immobilized thereon. The second antibody 26 is bound to an antigenic site of a target microorganism 32 and a different antibody 22 (referred to herein as a first antibody) is bound to a second antigenic site of the target microorganism 32. The first antibody 22 is conjugated to a reporter compound 30 as described above. After the permeable membrane 10 is washed, a detection solution, as described above, is added to the permeable membrane 10 which changes the color of the permeable membrane 10 in locations where the target microorganism 32 is attached to the permeable membrane 10 via binding to the immobilized antibody 26.

Figure 5:
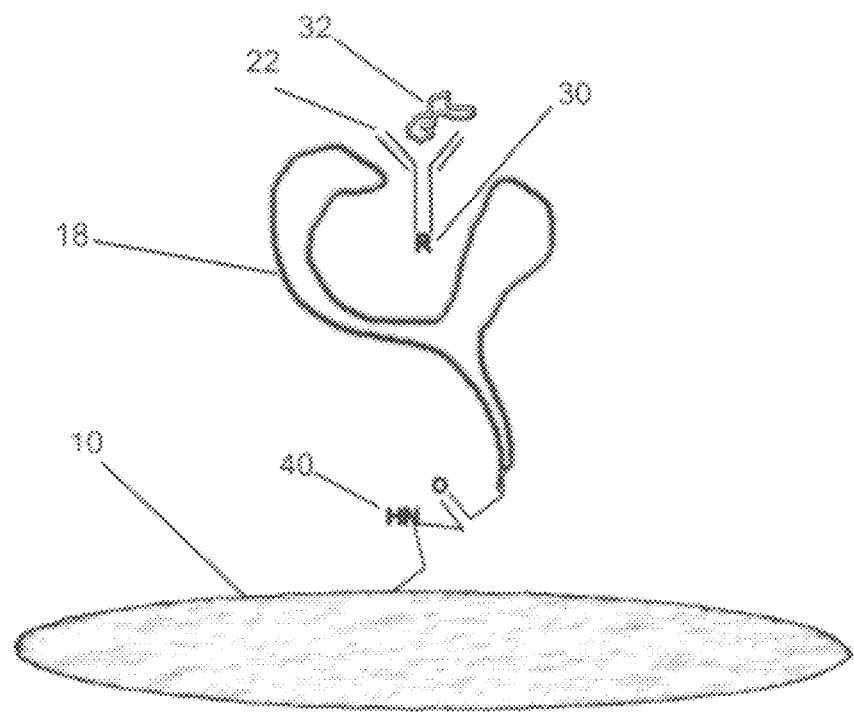
FIG. 5 shows an antibody (referred to herein as a first antibody) bound by an aptamer (referred to herein as a second aptamer), the first antibody conjugated to a reporter compound and bound to a target microorganism. The second aptamer is immobilized on a permeable membrane via linkage to an amine compound.

Referring to FIG. 5, a permeable membrane 10 is shown with an aptamer 18 (referred to herein as a second aptamer) immobilized thereon. The aptamer 18 is linked to an amine compound 40 which immobilizes the second aptamer 18 to the permeable membrane 10. The second aptamer 18 is bound to an antibody 22 (referred to herein as a first antibody), which is bound to a target microorganism 32. The first antibody 22 is conjugated to a reporter compound as described above. After the permeable membrane 10 is washed, a detection solution, as described above, is added to the permeable membrane 10 which changes the color of the permeable membrane 10 in locations where the target microorganism 32 is attached to the permeable membrane 10 via binding to the immobilized second aptamer 18.

Figure 6:
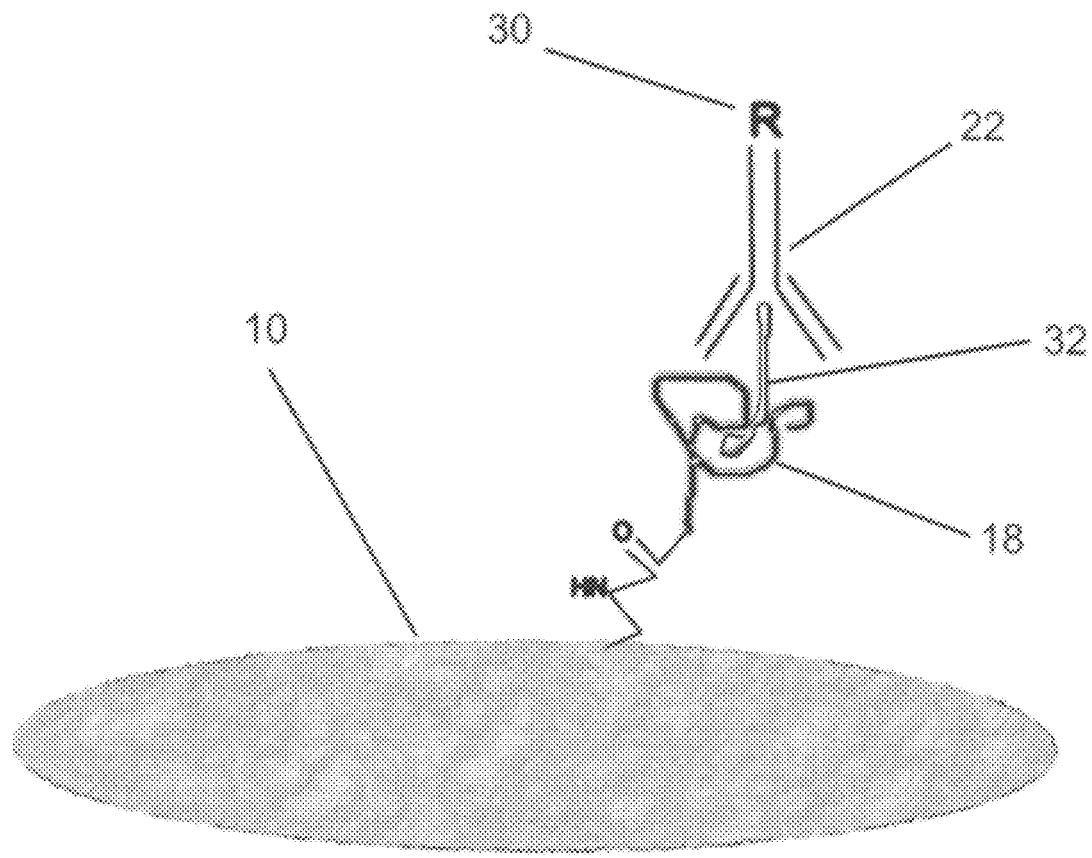
FIG. 6 shows an antibody (referred to herein as a first antibody) bound to one site of a target microorganism, the first antibody conjugated to a reporter compound, and a permeable membrane having an immobilized aptamer thereon (referred to herein as a second aptamer). The second aptamer is bound to a second site of the target microorganism and is immobilized on the permeable membrane via linkage to an amine compound.

Referring to FIG. 6, a permeable membrane 10 is shown with an aptamer 18 (referred to herein as a second aptamer) immobilized thereon. The second aptamer 18 is linked to an amine compound which immobilizes the second aptamer 18 to the permeable membrane 10. The second aptamer 18 is bound to one site of a target microorganism 32 and an antibody 22 (referred to herein as a first antibody) is bound to a different antigenic site of the target microorganism 32. The first antibody 22 is conjugated to a reporter compound 30 as described above. After the permeable membrane 10 is washed, a detection solution, as described above, is added to the permeable membrane 10 which changes the color of the permeable membrane 10 in locations where the target microorganism 32 is attached to the permeable membrane 10 via binding to the immobilized second aptamer 18.

Figure 7:
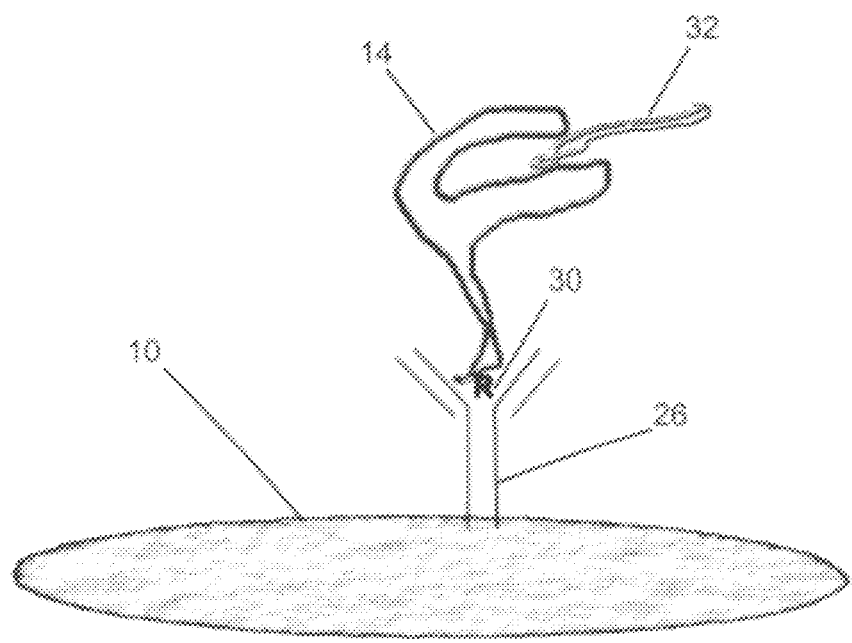
FIG. 7 shows an aptamer (referred to herein as a first aptamer) bound by an antibody (referred to herein as a second antibody), the first aptamer conjugated to a reporter compound and bound to a target microorganism. The second antibody is immobilized on a permeable membrane.

Referring to FIG. 7, a permeable membrane 10 is shown with an antibody 26 (referred to herein as a second antibody) immobilized thereon. The second antibody 26 is bound to an aptamer 14 (referred to herein as a first aptamer), which is bound to a target microorganism 32. The first aptamer 14 is conjugated to a reporter compound as described above. After the permeable membrane 10 is washed, a detection solution, as described above, is added to the permeable membrane 10 which changes the color of the permeable membrane 10 in locations where the target microorganism 32 is attached to the permeable membrane 10 via binding to the immobilized second antibody 26.

Figure 8:
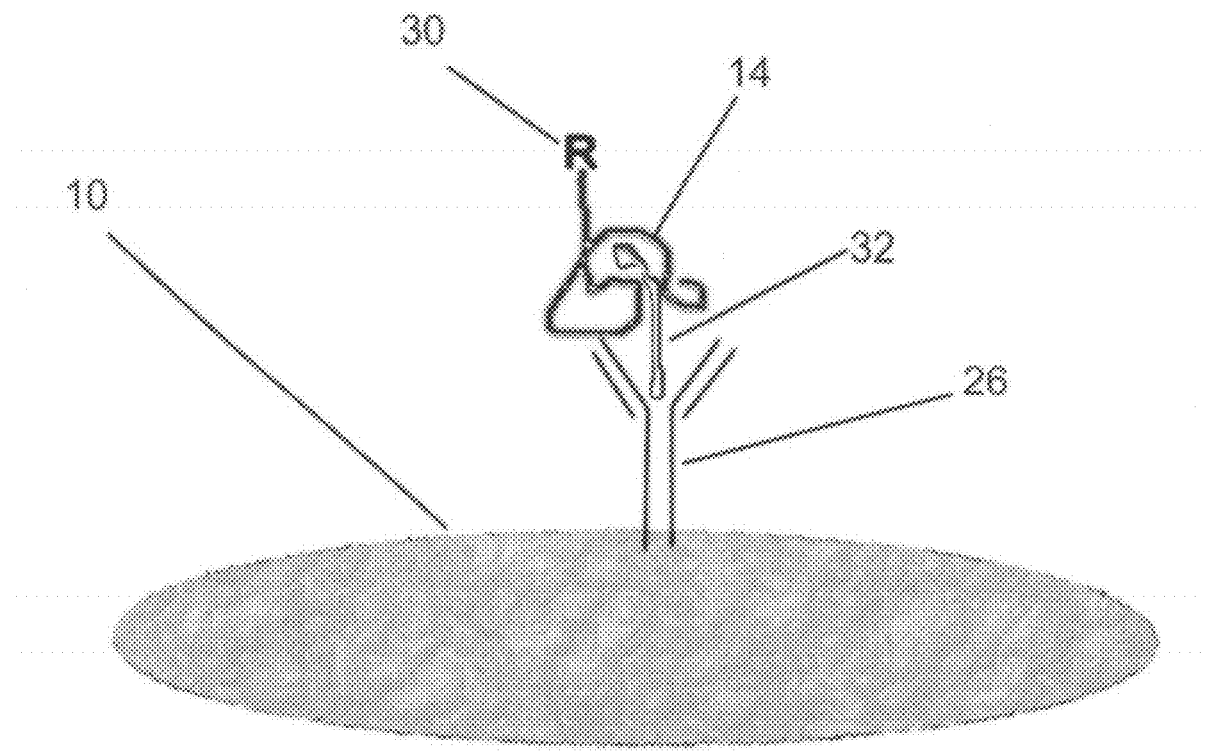
FIG. 8 shows an aptamer (referred to herein as a first aptamer) bound to one site of a target microorganism, the first aptamer conjugated to a reporter compound, and a permeable membrane having an immobilized antibody thereon (referred to herein as a second antibody). The second antibody is bound to a second site of the target microorganism.

Referring to FIG. 8, a permeable membrane 10 is shown with an antibody 26 (referred to herein as a second antibody) immobilized thereon. The second antibody 26 is bound to an antigenic site of a target microorganism 32 and an aptamer 14 (referred to herein as a first aptamer) is bound to a different site of the target microorganism 32. The first aptamer 14 is conjugated to a reporter compound 30 as described above. After the permeable membrane 10 is washed, a detection solution, as described above, is added to the membrane 10 which changes the color of the permeable membrane 10 in locations where the target microorganism 32 is attached to the permeable membrane 10 via binding to the immobilized second antibody 26.

The present invention encompasses not only the foregoing described configurations of aptamers and/or antibodies, but also encompasses having more than one type of aptamer and/or more than one type of antibody immobilized on the permeable membrane and more than one type of aptamer and/or more than one type of antibody conjugated to a reporter compound, in order to allow for rapid detection and identification of more than one target microorganism.

EXAMPLES

The present invention is more particularly described in the following non-limiting examples, which are intended to be illustrative only, as numerous modifications and variations therein will be apparent to those skilled in the art.

Example 1

Rapid Detection and Identification of Group B *Streptococcus* (GBS) Using Aptamers as Reporter and Capture Compounds A liquid sample containing an unknown number of live bacterial species including the target bacterium GBS (also known as *Streptococcus agalactiae*) is set up as described below. Alternatively, a sample containing an unknown mixture of live bacterial species including the target bacterium GBS is poured on a Petri plate filled with sheep blood agar (SBA); the plate is incubated at a temperature of about 37° C. for about 3 to 6 hours to grow the bacteria; and, after the bacterial species is grown and microcolonies appear, a sample specimen of the microcolonies is set up as described below. A 0.5 McFarland of the liquid sample or, alternatively, a sample of the grown microcolonies, is prepared as commonly known in the art and the bacteria are serially diluted, starting at about $10^5$ bacteria/ml. To each dilution, a 1:30 dilution of horseradish peroxidase (HRP) conjugated to aptamers selected against GBS is added to bring the final volume up to 100 ml. The sample is spun at 3,000 rpm in a microcentrifuge and washed with phosphate buffered saline (PBS) three times. The pellet is resuspended in PBS. Twenty ml of the resuspended sample is added to a nitrocellulose permeable membrane which has been blocked overnight with 1% bovine serum albumin blocking compounds and containing immobilized aptamers (linked via amine compounds to the membrane) selected to bind to the aptamers conjugated with HRP. The permeable membrane then is washed three times. A drop of 3,3'-diaminobenzidine (DAB) (3 mg/ml in Tris saline buffer, pH 7.6), 3% $H_2O_2$ and 1.2 weight % of $NiCl_2$ then is added to the permeable membrane. A color reaction to a grey-brown color rapidly develops in about 0.5 to 3 minutes on the surface of the permeable membrane in locations where GBS is attached to the membrane via binding to the immobilized aptamers. GBS then is detected and identified on the permeable membrane due to the color change of the GBS microcolony(ies), which is distinguished from the color of any other species of bacteria contained in the mixture. GBS is detected reliably at $10^5$ to $10^2$ bacteria/ml in as little as 30 minutes, with minimal background observed, and with no cross-reactivity to other species of bacteria. This detection and identification assay is significantly more rapid than any other microbiological diagnostic assay known to date.

Example 2

Rapid Detection and Identification of GBS Using Aptamers as Reporter and Capture Compounds and Selected Against Two Different Sites of GBS A liquid sample containing an unknown number of live bacterial species including the target bacterium GBS is set up as described below. Alternatively, a sample containing an unknown mixture of live bacterial species including the target bacterium GBS is poured on a Petri plate filled with SBA; the plate is incubated at a temperature of about 37° C. for about 3 to 6 hours to grow the bacteria; and, after the bacterial species is grown and microcolonies appear, a sample specimen of the microcolonies is set up as described below. A 0.5 McFarland of the liquid sample or, alternatively, a sample of the grown microcolonies, is prepared as commonly known in the art and the bacteria are serially diluted, starting at about $10^5$ bacteria/ml. To each dilution, a 1:30 dilution of HRP conjugated to aptamers selected against one antigenic site of GBS is added to bring the final volume up to 20 ml. The 20 ml sample is added to a nitrocellulose permeable membrane which has been blocked overnight with 1% BSA blocking compounds and containing immobilized aptamers (linked via amine compounds to the membrane) selected to bind to a second antigenic site of GBS. The permeable membrane then is washed in a washing solution (PBS, pH 7.4 with 0.1% Tween 20) using a portable washing device at medium speed of rotation for about two minutes. A drop of DAB (3 mg/ml in Tris saline buffer, pH 7.6), 3% $H_2O_2$ and 1.2 weight % of $NiCl_2$ then is added to the permeable membrane. A color reaction to a grey-brown color rapidly develops in about 0.5 to 3 minutes on the surface of the permeable membrane in locations where GBS is attached to the membrane via binding to the immobilized aptamers. GBS then is detected and identified on the permeable membrane due to the color change of the GBS microcolony(ies), which is distinguished from the color of any other species of bacteria contained in the mixture. GBS is detected reliably at $10^5$ to $10^2$ bacteria/ml in as little as 30 minutes, with minimal background observed, and with no cross-reactivity to other species of bacteria. This detection and identification assay is significantly more rapid than any other microbiological diagnostic assay known to date.

Example 3

Rapid Detection and Identification of GBS Using Antibodies as Reporter and Capture Compounds A liquid sample containing an unknown number of live bacterial species including the target bacterium GBS is set up as described below. Alternatively, a sample containing an unknown mixture of live bacterial species including the target bacterium GBS is poured on a Petri plate filled with SBA; the plate is incubated at a temperature of about 37° C. for about 3 to 6 hours to grow the bacteria; and, after the bacterial species is grown and microcolonies appear, a sample specimen of the microcolonies is set up as described below. A 0.5 McFarland of the liquid sample or, alternatively, a sample of the grown microcolonies, is prepared as commonly known in the art and the bacteria are serially diluted, starting at about $10^5$ bacteria/ml. To each dilution, a 1:30 dilution of HRP conjugated to rabbit polyclonal antibodies against GBS is added to bring the final volume up to 100 ml. The sample is spun at 3,000 rpm in a microcentrifuge and washed with PBS three times. The pellet is resuspended in PBS. Twenty ml of the resuspended sample is added to a nitrocellulose permeable membrane which has been coated with 20 ml of a 1:40 dilution of mouse monoclonal antibody against rabbit IgG and blocked overnight with 1% BSA blocking compounds. The permeable membrane then is washed three times. A drop of DAB (3 mg/ml in Tris saline buffer, pH 7.6), 3% $H_2O_2$ and 1.2 weight % of $NiCl_2$ then is added to the permeable membrane. A color reaction to a grey-brown color rapidly develops in about 0.5 to 3 minutes on the surface of the permeable membrane in locations where GBS is attached to the membrane via binding to the immobilized antibodies. GBS then is detected and identified on the permeable membrane due to the color change of the GBS microcolony(ies), which is distinguished from the color of any other species of bacteria contained in the mixture. GBS is detected reliably at $10^5$ to $10^2$ bacteria/ml in as little as 30 minutes, with minimal background observed, and with no cross-reactivity to other species of bacteria. This detection and identification assay is significantly more rapid than any other microbiological diagnostic assay known to date.

Example 4

Rapid Detection and Identification of GBS Using Antibodies as Reporter and Capture Compounds and Selected Against Two Different Sites of GBS A liquid sample containing an unknown number of live bacterial species including the target bacterium GBS is set up as described below. Alternatively, a sample containing an unknown mixture of live bacterial species including the target bacterium GBS is poured on a Petri plate filled with SBA; the plate is incubated at a temperature of about 37° C. for about 3 to 6 hours to grow the bacteria; and, after the bacterial species is grown and microcolonies appear, a sample specimen of the microcolonies is set up as described below. A 0.5 McFarland of the liquid sample or, alternatively, a sample of the grown microcolonies, is prepared as commonly known in the art and the bacteria are serially diluted, starting at about $10^5$ bacteria/ml. To each dilution, a 1:30 dilution of HRP conjugated to rabbit polyclonal antibodies specific for an antigenic site of GBS is added to bring the final volume up to 20 ml. The 20 ml sample is added to a nitrocellulose permeable membrane which has been coated with 20 ml of a 1:40 dilution of rabbit polyclonal antibodies specific for a different antigenic site of GBS and blocked overnight with 1% BSA blocking compounds. The permeable membrane then is washed in a washing solution (PBS, pH 7.4 with 0.1% Tween 20) using a portable washing device at medium speed of rotation for about two minutes. A drop of DAB (3 mg/ml in Tris saline buffer, pH 7.6), 3% $H_2O_2$ and 1.2 weight % of $NiCl_2$ then is added to the permeable membrane. A color reaction to a grey-brown color rapidly develops in about 0.5 to 3 minutes on the surface of the permeable membrane in locations where GBS is attached to the membrane via binding to the immobilized aptamers. GBS then is detected and identified on the permeable membrane due to the color change of the GBS microcolony(ies), which is distinguished from the color of any other species of bacteria contained in the mixture. GBS is detected reliably at $10^5$ to $10^2$ bacteria/ml in as little as 30 minutes, with minimal background observed, and with no cross-reactivity to other species of bacteria. This detection and identification assay is significantly more rapid than any other microbiological diagnostic assay known to date.

Example 5

Rapid Detection and Identification of *Bacillus Anthracia* (Anthrax) Using Aptamers as Reporter and Capture Compounds A liquid sample containing an unknown number of live bacterial species including the target bacterium anthrax is set up as described below. Alternatively, a sample containing an unknown mixture of live bacterial species including the target bacterium anthrax is poured on a Petri plate filled with SBA; the plate is incubated at a temperature of about 37° C. for about 3 to 6 hours to grow the bacteria; and, after the bacterial species is grown and microcolonies appear, a sample specimen of the microcolonies is set up as described below. A 0.5 McFarland of the liquid sample or, alternatively, a sample of the grown microcolonies, is prepared as commonly known in the art and the bacteria are serially diluted, starting at about $10^5$ bacteria/ml. To each dilution, a 1:30 dilution of HRP conjugated to aptamers selected against anthrax is added to bring the final volume up to 100 ml. The sample is spun at 3,000 rpm in a microcentrifuge and washed with PBS three times. The pellet is resuspended in PBS. Twenty ml of the resuspended sample is added to a nitrocellulose permeable membrane which has been blocked overnight with 1% BSA blocking compounds and containing immobilized aptamers (linked to amine linker compounds) selected to bind to the aptamers conjugated with HRP. The permeable membrane then is washed three times. A drop of DAB (3 mg/ml in Tris saline buffer, pH 7.6), 3% $H_2O_2$ and 1.2 weight % of $NiCl_2$ then is added to the permeable membrane. A color reaction to a grey-brown color rapidly develops in about 0.5 to 3 minutes on the surface of the permeable membrane in locations where anthrax is attached to the membrane via binding to the immobilized aptamers. Anthrax then is detected and identified on the permeable membrane due to the color change of the anthrax microcolony(ies), which is distinguished from the color of any other species of bacteria contained in the mixture. Anthrax is detected reliably at $10^5$ to $10^2$ bacteria/ml in as little as 30 minutes, with minimal background observed, and with no cross-reactivity to other species of bacteria. This detection and identification assay is significantly more rapid than any other microbiological diagnostic assay known to date.

Example 6

Rapid Detection and Identification of Anthrax Using Aptamers as Reporter and Capture Compounds and Selected Against Two Different Sites of *Bacillus Anthracia*

A liquid sample containing an unknown number of live bacterial species including the target bacterium anthrax is set up as described below. Alternatively, a sample containing an unknown mixture of live bacterial species including the target bacterium anthrax is poured on a Petri plate filled with SBA; the plate is incubated at a temperature of about 37° C. for about 3 to 6 hours to grow the bacteria; and, after the bacterial species is grown and microcolonies appear, a sample specimen of the microcolonies is set up as described below. A 0.5 McFarland of the liquid sample or, alternatively, a sample of the grown microcolonies, is prepared as commonly known in the art and the bacteria are serially diluted, starting at about $10^5$ bacteria/ml. To each dilution, a 1:30 dilution of HRP conjugated to aptamers selected against one antigenic site of anthrax is added to bring the final volume up to 20 ml. The 20 ml sample is added to a nitrocellulose permeable membrane which has been blocked overnight with 1% BSA blocking compounds and containing immobilized aptamers (linked via amine compounds to the membrane) selected to bind to a second antigenic site of anthrax. The permeable membrane then is washed in a washing solution (PBS, pH 7.4 with 0.1% Tween 20) using a portable washing device at medium speed of rotation for about two minutes. A drop of DAB (3 mg/ml in Tris saline buffer, pH 7.6), 3% $H_2O_2$ and 1.2 weight % of $NiCl_2$ then is added to the permeable membrane. A color reaction to a grey-brown color rapidly develops in about 0.5 to 3 minutes on the surface of the permeable membrane in locations where anthrax is attached to the membrane via binding to the immobilized aptamers. Anthrax then is detected and identified on the permeable membrane due to the color change of the anthrax microcolony(ies), which is distinguished from the color of any other species of bacteria contained in the mixture. Anthrax is detected reliably at $10^5$ to $10^2$ bacteria/ml in as little as 30 minutes, with minimal background observed, and with no cross-reactivity to other species of bacteria. This detection and identification assay is significantly more rapid than any other microbiological diagnostic assay known to date.

Example 7

Rapid Detection and Identification of Anthrax Using Antibodies as Reporter and Capture Compounds A liquid sample containing an unknown number of live bacterial species including the target bacterium anthrax is set up as described below. Alternatively, a sample containing an unknown mixture of live bacterial species including the target bacterium GBS is poured on a Petri plate filled with SBA; the plate is incubated at a temperature of about 37° C. for about 3 to 6 hours to grow the bacteria; and, after the bacterial species is grown and microcolonies appear, a sample specimen of the microcolonies is set up as described below. A 0.5 McFarland of the liquid sample or, alternatively, a sample of the grown microcolonies, is prepared as commonly known in the art and the bacteria are serially diluted, starting at about $10^5$ bacteria/ml. To each dilution, a 1:30 dilution of HRP conjugated to rabbit polyclonal antibodies against anthrax is added to bring the final volume up to 100 ml. The sample is spun at 3,000 rpm in a microcentrifuge and washed with PBS three times. The pellet is resuspended in PBS. Twenty ml of the resuspended sample is added to a nitrocellulose permeable membrane which has been coated with 20 ml of a 1:40 dilution of mouse monoclonal antibody against rabbit IgG and blocked overnight with 1% BSA blocking compounds. The permeable membrane then is washed three times. A drop of DAB (3 mg/ml in Tris saline buffer, pH 7.6), 3% $H_2O_2$ and 1.2 weight % of $NiCl_2$ then is added to the permeable membrane. A color reaction to a grey-brown color rapidly develops in about 0.5 to 3 minutes on the surface of the permeable membrane in locations where anthrax is attached to the membrane via binding to the immobilized antibodies. Anthrax then is detected and identified on the permeable membrane due to the color change of the anthrax microcolony(ies), which is distinguished from the color of any other species of bacteria contained in the mixture. Anthrax is detected reliably at $10^5$ to $10^2$ bacteria/ml in as little as 30 minutes, with minimal background observed, and with no cross-reactivity to other species of bacteria. This detection and identification assay is significantly more rapid than any other microbiological diagnostic assay known to date.

Example 8

Rapid Detection and Identification of Anthrax Using Antibodies as Reporter and Capture Compounds and Selected Against Two Different Sites of Anthrax A liquid sample containing an unknown number of live bacterial species including the target bacterium anthrax is set up as described below. Alternatively, a sample containing an unknown mixture of live bacterial species including the target bacterium anthrax is poured on a Petri plate filled with SBA; the plate is incubated at a temperature of about 37° C. for about 3 to 6 hours to grow the bacteria; and, after the bacterial species is grown and microcolonies appear, a sample specimen of the microcolonies is set up as described below. A 0.5 McFarland of the liquid sample or, alternatively, a sample of the grown microcolonies, is prepared as commonly known in the art and the bacteria are serially diluted, starting at about $10^5$ bacteria/ml. To each dilution, a 1:30 dilution of HRP conjugated to rabbit polyclonal antibodies specific for an antigenic site of anthrax is added to bring the final volume up to 20 ml. The 20 ml sample is added to a nitrocellulose permeable membrane which has been coated with 20 ml of a 1:40 dilution of rabbit polyclonal antibodies specific for a different antigenic site of anthrax and blocked overnight with 1% BSA blocking compounds. The permeable membrane then is washed in a washing solution (PBS, pH 7.4 with 0.1% Tween 20) using a portable washing device at medium speed of rotation for about two minutes. A drop of DAB (3 mg/ml in Tris saline buffer, pH 7.6), 3% $H_2O_2$ and 1.2 weight % of $NiCl_2$ then is added to the permeable membrane. A color reaction to a grey-brown color rapidly develops in about 0.5 to 3 minutes on the surface of the permeable membrane in locations where anthrax is attached to the membrane via binding to the immobilized antibodies. Anthrax then is detected and identified on the permeable membrane due to the color change of the anthrax microcolony(ies), which is distinguished from the color of any other species of bacteria contained in the mixture. Anthrax is detected reliably at $10^5$ to $10^2$ bacteria/ml in as little as 30 minutes, with minimal background observed, and with no cross-reactivity to other species of bacteria. This detection and identification assay is significantly more rapid than any other microbiological diagnostic assay known to date.

Example 9

Rapid Detection and Identification of *Escherichia coli* O157 H:7 (*E. coli*) and *Salmonella* Using Aptamers as Reporter and Capture Compounds A liquid sample containing an unknown number of live bacterial species including the two target bacteria *E. coli* and *Salmonella* is set up as described below. Alternatively, a sample containing an unknown mixture of live bacterial species including the two target bacteria *E. coli* and *Salmonella* are poured on a Petri plate filled with SBA; the plate is incubated at a temperature of about 37° C. for about 3 to 6 hours to grow the bacteria; and, after the bacterial species is grown and microcolonies appear, a sample specimen of the microcolonies is set up as described below. A 0.5 McFarland of the liquid sample or, alternatively, a sample of the grown microcolonies, is prepared as commonly known in the art and the bacteria are serially diluted, starting at about $10^5$ bacteria/ml. To each dilution, a 1:30 dilution of HRP conjugated to aptamers selected against *E. coli* and aptamers selected against *Salmonella* is added to bring the final volume up to 100 ml. The sample is spun at 3,000 rpm in a microcentrifuge and washed with PBS three times. The pellet is resuspended in PBS. Twenty ml of the resuspended sample is added to a nitrocellulose permeable membrane which has been blocked overnight with 1% BSA blocking compounds and containing immobilized thereon two different aptamers (each linked via amine compounds to the membrane). The first aptamer is selected to bind to the aptamers conjugated with HRP and selected against *E. coli* and the second aptamer is selected to bind to the aptamers conjugated with HRP and selected against *Salmonella*. The two different aptamers are localized on the permeable membrane in distinct locations to distinguish between the two species of bacteria. The permeable membrane then is washed three times. A drop of DAB (3 mg/ml in Tris saline buffer, pH 7.6), 3% $H_2O_2$ and 1.2 weight % of $NiCl_2$ then is added to the permeable membrane. A color reaction to a grey-brown color rapidly develops in about 0.5 to 3 minutes on the surface of the permeable membrane in locations where *E. coli* and *Salmonella* are attached to the membrane via binding to their respective immobilized aptamers. *E. coli* and *Salmonella* then are detected and identified on the permeable membrane due to the color change of the *E. coli* and *Salmonella* on the permeable membrane and their respective locations on the permeable membrane, which is distinguished from the color of any other species of bacteria which may be contained in the mixture. *E. coli* and *Salmonella* are detected reliably at $10^5$ to $10^2$ bacteria/ml in as little as 30 minutes, with minimal background observed, and with no cross-reactivity to other species of bacteria. This detection and identification assay is significantly more rapid than any other microbiological diagnostic assay known to date.

Example 10

Rapid Detection and Identification of *E. coli* and *Salmonella* Using Aptamers as Reporter and Capture Compounds and Selected Against Two Different Sites of *E. coli* and *Salmonella*

A liquid sample containing an unknown number of live bacterial species including the two target bacteria *E. coli* and *Salmonella* is set up as described below. Alternatively, a sample containing an unknown mixture of live bacterial species including the two target bacteria *E. coli* and *Salmonella* are poured on a Petri plate filled with SBA; the plate is incubated at a temperature of about 37° C. for about 3 to 6 hours to grow the bacteria; and, after the bacterial species is grown and microcolonies appear, a sample specimen of the microcolonies is set up as described below. A 0.5 McFarland of the liquid sample or, alternatively, a sample of the grown microcolonies, is prepared as commonly known in the art and the bacteria are serially diluted, starting at about $10^5$ bacteria/ml. To each dilution, a 1:30 dilution of HRP conjugated to two different aptamers, one aptamer selected for a first antigenic site of *E. coli* and the other aptamer selected for a first antigenic site of *Salmonella*, is added to bring the final volume up to 20 ml. The 20 ml sample is added to a nitrocellulose permeable membrane which has been blocked overnight with 1% BSA blocking compounds and which has been coated with 20 ml of a 1:40 dilution of two aptamers (each linked via an amine compound to the membrane), the first aptamer selected for a second antigenic site of *E. coli* and the second aptamer selected for a second antigenic site of *Salmonella*. The permeable membrane then is washed in a washing solution (PBS, pH 7.4 with 0.1% Tween 20) using a portable washing device at medium speed of rotation for about two minutes. A drop of DAB (3 mg/ml in Tris saline buffer, pH 7.6), 3% $H_2O_2$ and 1.2 weight % of $NiCl_2$ then is added to the permeable membrane. A color reaction to a grey-brown color rapidly develops in about 0.5 to 3 minutes on the surface of the permeable membrane in locations where *E. coli* and *Salmonella* are attached to the membrane via binding to their respective immobilized aptamers. *E. coli* and *Salmonella* then are detected and identified on the permeable membrane due to the color change of the *E. coli* and *Salmonella* on the permeable membrane and their respective locations on the permeable membrane, which is distinguished from the color of any other species of bacteria which may be contained in the mixture. *E. coli* and *Salmonella* are detected reliably at $10^5$ to $10^2$ bacteria/ml in as little as 30 minutes, with minimal background observed, and with no cross-reactivity to other species of bacteria. This detection and identification assay is significantly more rapid than any other microbiological diagnostic assay known to date.

Example 11

Rapid Detection and Identification of *E. coli* and *Salmonella* Using Antibodies as Reporter and Capture Compounds A liquid sample containing an unknown number of live bacterial species including the two target bacteria *E. coli* and *Salmonella* is set up as described below. Alternatively, a sample containing an unknown mixture of live bacterial species including the two target bacteria *E. coli* and *Salmonella* are poured on a Petri plate filled with SBA; the plate is incubated at a temperature of about 37° C. for about 3 to 6 hours to grow the bacteria; and, after the bacterial species is grown and microcolonies appear, a sample specimen of the microcolonies is set up as described below. A 0.5 McFarland of the liquid sample or, alternatively, a sample of the grown microcolonies, is prepared as commonly known in the art and the bacteria are serially diluted, starting at about $10^5$ bacteria/ml. To each dilution, a 1:30 dilution of HRP conjugated to antibodies specific for an antigenic site of *E. coli* and antibodies specific for an antigenic site of *Salmonella* is added to bring the final volume up to 100 ml. The sample is spun at 3,000 rpm in a microcentrifuge and washed with PBS three times. The pellet is resuspended in PBS. Twenty ml of the resuspended sample is added to a nitrocellulose permeable membrane which has been blocked overnight with 1% BSA blocking compounds and containing immobilized thereon two different antibodies. The first antibody is specific to an antigenic site of the antibodies conjugated with HRP and specific to an antigenic site of E. coli and the second antibody is specific to an antigenic site of the antibodies conjugated with HRP and specific to an antigenic site of Salmonella. The two different antibodies are localized on the permeable membrane in distinct locations to distinguish between the two species of bacteria. The permeable membrane then is washed three times. A drop of DAB (3 mg/ml in Tris saline buffer, pH 7.6), 3% $H_2O_2$ and 1.2 weight % of $NiCl_2$ then is added to the permeable membrane. A color reaction to a grey-brown color rapidly develops in about 0.5 to 3 minutes on the surface of the permeable membrane in locations where E. coli and Salmonella are attached to the membrane via binding to their respective immobilized antibodies. E. coli and Salmonella then are detected and identified on the permeable membrane due to the color change of the E. coli and Salmonella on the permeable membrane and their respective locations on the permeable membrane, which is distinguished from the color of any other species of bacteria which may be contained in the mixture. E. coli and Salmonella are detected reliably at $10^5$ to $10^2$ bacteria/ml in as little as 30 minutes, with minimal background observed, and with no cross-reactivity to other species of bacteria. This detection and identification assay is significantly more rapid than any other microbiological diagnostic assay known to date.

Example 12

Rapid Detection and Identification of E. coli and Salmonella Using Antibodies as Reporter and Capture Compounds and Selected Against Two Different Sites of E. coli and Salmonella A liquid sample containing an unknown number of live bacterial species including the two target bacteria E. coli and Salmonella is set up as described below. Alternatively, a sample containing an unknown mixture of live bacterial species including the two target bacteria E. coli and Salmonella are poured on a Petri plate filled with SBA; the plate is incubated at a temperature of about 37° C. for about 3 to 6 hours to grow the bacteria; and, after the bacterial species is grown and microcolonies appear, a sample specimen of the microcolonies is set up as described below. A 0.5 McFarland of the liquid sample or, alternatively, a sample of the grown microcolonies, is prepared as commonly known in the art and the bacteria are serially diluted, starting at about $10^5$ bacteria/ml. To each dilution, a 1:30 dilution of HRP conjugated to two different rabbit polyclonal antibodies, one antibody specific for a first antigenic site of E. coli and the other antibody specific for a first antigenic site of Salmonella, is added to bring the final volume up to 20 ml. The 20 ml sample is added to a nitrocellulose permeable membrane which has been blocked overnight with 1% BSA blocking compounds and which has been coated with 20 ml of a 1:40 dilution of two rabbit polyclonal antibodies, the first antibody specific for a second antigenic site of E. coli and the second antibody specific for a second antigenic site of Salmonella. The permeable membrane then is washed in a washing solution (PBS, pH 7.4 with 0.1% Tween 20) using a portable washing device at medium speed of rotation for about two minutes. A drop of DAB (3 mg/ml in Tris saline buffer, pH 7.6), 3% $H_2O_2$ and 1.2 weight % of $NiCl_2$ then is added to the permeable membrane. A color reaction to a grey-brown color rapidly develops in about 0.5 to 3 minutes on the surface of the permeable membrane in locations where E. coli and Salmonella are attached to the membrane via binding to their respective immobilized antibodies. E. coli and Salmonella then are detected and identified on the permeable membrane due to the color change of the E. coli and Salmonella on the permeable membrane and their respective locations on the permeable membrane, which is distinguished from the color of any other species of bacteria which may be contained in the mixture. E. coli and Salmonella are detected reliably at $10^5$ to $10^2$ bacteria/ml in as little as 30 minutes, with minimal background observed, and with no cross-reactivity to other species of bacteria. This detection and identification assay is significantly more rapid than any other microbiological diagnostic assay known to date.

Example 13

Rapid Detection and Identification of E. coli and Salmonella Using Aptamers and Antibodies as Reporter Compounds and Aptamers as Capture Compounds A liquid sample containing an unknown number of live bacterial species including the two target bacteria E. coli and Salmonella is set up as described below. Alternatively, a sample containing an unknown mixture of live bacterial species including the two target bacteria E. coli and Salmonella are poured on a Petri plate filled with SBA; the plate is incubated at a temperature of about 37° C. for about 3 to 6 hours to grow the bacteria; and, after the bacterial species is grown and microcolonies appear, a sample specimen of the microcolonies is set up as described below. A 0.5 McFarland of the liquid sample or, alternatively, a sample of the grown microcolonies, is prepared as commonly known in the art and the bacteria are serially diluted, starting at about $10^5$ bacteria/ml. To each dilution, a 1:30 dilution of HRP conjugated to aptamers selected against E. coli and antibodies specific for an antigenic site of Salmonella is added to bring the final volume up to 100 ml. The sample is spun at 3,000 rpm in a microcentrifuge and washed with PBS three times. The pellet is resuspended in PBS. Twenty ml of the resuspended sample is added to a nitrocellulose permeable membrane which has been blocked overnight with 1% BSA blocking compounds and containing immobilized thereon two different aptamers (each linked to amine compounds). The first aptamer is selected to bind to the aptamer conjugated with HRP and selected against E. coli and the second aptamer is selected to bind to the antibodies conjugated with HRP and specific for an antigenic site of Salmonella. The two different aptamers are localized on the permeable membrane in distinct locations to distinguish between the two species of bacteria. The permeable membrane then is washed three times. A drop of DAB (3 mg/ml in Tris saline buffer, pH 7.6), 3% $H_2O_2$ and 1.2 weight % of $NiCl_2$ then is added to the permeable membrane. A color reaction to a grey-brown color rapidly develops in about 0.5 to 3 minutes on the surface of the permeable membrane in locations where E. coli and Salmonella are attached to the membrane via binding to their respective immobilized aptamers. E. coli and Salmonella then are detected and identified on the permeable membrane due to the color change of the E. coli and Salmonella on the permeable membrane and their respective locations on the permeable membrane, which is distinguished from the color of any other species of bacteria which may be contained in the mixture. E. coli and Salmonella are detected reliably at $10^5$ to $10^2$ bacteria/ml in as little as 30 minutes, with minimal background observed, and with no cross-reactivity to other species of bacteria. This detection and identification assay is significantly more rapid than any other microbiological diagnostic assay known to date.

Example 14

Rapid Detection and Identification of *E. coli* and *Salmonella* Using Aptamers and Antibodies as Reporter Compounds and Aptamers as Capture Compounds and Selected Against Two Different Sites of *E. coli* and *Salmonella*

A liquid sample containing an unknown number of live bacterial species including the two target bacteria *E. coli* and *Salmonella* is set up as described below. Alternatively, a sample containing an unknown mixture of live bacterial species including the two target bacteria *E. coli* and *Salmonella* are poured on a Petri plate filled with SBA; the plate is incubated at a temperature of about 37° C. for about 3 to 6 hours to grow the bacteria; and, after the bacterial species is grown and microcolonies appear, a sample specimen of the microcolonies is set up as described below. A 0.5 McFarland of the liquid sample or, alternatively, a sample of the grown microcolonies, is prepared as commonly known in the art and the bacteria are serially diluted, starting at about $10^5$ bacteria/ml. To each dilution, a 1:30 dilution of HRP conjugated to an aptamer selected for a first antigenic site of *E. coli* and an antibody specific for a first antigenic site of *Salmonella*, is added to bring the final volume up to 20 ml. The 20 ml sample is added to a nitrocellulose permeable membrane which has been blocked overnight with 1% BSA blocking compounds and which has been coated with 20 ml of a 1:40 dilution of two aptamers (each linked via an amine compound to the membrane), the first aptamer selected for a second antigenic site of *E. coli* and the second aptamer selected for a second antigenic site of *Salmonella*. The permeable membrane then is washed in a washing solution (PBS, pH 7.4 with 0.1% Tween 20) using a portable washing device at medium speed of rotation for about two minutes. A drop of DAB (3 mg/ml in Tris saline buffer, pH 7.6), 3% $H_2O_2$ and 1.2 weight % of $NiCl_2$ then is added to the permeable membrane. A color reaction to a grey-brown color rapidly develops in about 0.5 to 3 minutes on the surface of the permeable membrane in locations where *E. coli* and *Salmonella* are attached to the membrane via binding to their respective immobilized aptamers. *E. coli* and *Salmonella* then are detected and identified on the permeable membrane due to the color change of the *E. coli* and *Salmonella* on the permeable membrane and their respective locations on the permeable membrane, which is distinguished from the color of any other species of bacteria which may be contained in the mixture. *E. coli* and *Salmonella* are detected reliably at $10^5$ to $10^2$ bacteria/ml in as little as 30 minutes, with minimal background observed, and with no cross-reactivity to other species of bacteria. This detection and identification assay is significantly more rapid than any other microbiological diagnostic assay known to date.

Example 15

Rapid Detection and Identification of *E. coli* and *Salmonella* Using Aptamers and Antibodies as Reporter Compounds and Antibodies as Capture Compounds A liquid sample containing an unknown number of live bacterial species including the two target bacteria *E. coli* and *Salmonella* is set up as described below. Alternatively, a sample containing an unknown mixture of live bacterial species including the two target bacteria *E. coli* and *Salmonella* are poured on a Petri plate filled with SBA; the plate is incubated at a temperature of about 37° C. for about 3 to 6 hours to grow the bacteria; and, after the bacterial species is grown and microcolonies appear, a sample specimen of the microcolonies is set up as described below. A 0.5 McFarland of the liquid sample or, alternatively, a sample of the grown microcolonies, is prepared as commonly known in the art and the bacteria are serially diluted, starting at about $10^5$ bacteria/ml. To each dilution, a 1:30 dilution of HRP conjugated to aptamers selected against *E. coli* and antibodies specific for an antigenic site of *Salmonella* is added to bring the final volume up to 100 ml. The sample is spun at 3,000 rpm in a microcentrifuge and washed with PBS three times. The pellet is resuspended in PBS. Twenty ml of the resuspended sample is added to a nitrocellulose permeable membrane which has been blocked overnight with 1% BSA blocking compounds and containing immobilized thereon two different antibodies. The first antibody is selected to bind to the aptamers conjugated with HRP and selected against *E. coli* and the second antibody is selected to bind to the antibodies conjugated with HRP and specific for an antigenic site of *Salmonella*. The two different antibodies are localized on the permeable membrane in distinct locations to distinguish between the two species of bacteria. The permeable membrane then is washed three times. A drop of DAB (3 mg/ml in Tris saline buffer, pH 7.6), 3% $H_2O_2$ and 1.2 weight % of $NiCl_2$ then is added to the permeable membrane. A color reaction to a grey-brown color rapidly develops in about 0.5 to 3 minutes on the surface of the permeable membrane in locations where *E. coli* and *Salmonella* are attached to the membrane via binding to their respective immobilized antibodies. *E. coli* and *Salmonella* then are detected and identified on the permeable membrane due to the color change of the *E. coli* and *Salmonella* on the permeable membrane and their respective locations on the permeable membrane, which is distinguished from the color of any other species of bacteria which may be contained in the mixture. *E. coli* and *Salmonella* are detected reliably at $10^5$ to $10^2$ bacteria/ml in as little as 30 minutes, with minimal background observed, and with no cross-reactivity to other species of bacteria. This detection and identification assay is significantly more rapid than any other microbiological diagnostic assay known to date.

Example 16

Rapid Detection and Identification of *E. coli* and *Salmonella* Using Aptamers and Antibodies as Reporter Compounds and Antibodies as Capture Compounds and Selected Against Two Different Sites of *E. coli* and *Salmonella*

A liquid sample containing an unknown number of live bacterial species including the two target bacteria *E. coli* and *Salmonella* is set up as described below. Alternatively, a sample containing an unknown mixture of live bacterial species including the two target bacteria *E. coli* and *Salmonella* are poured on a Petri plate filled with SBA; the plate is incubated at a temperature of about 37° C. for about 3 to 6 hours to grow the bacteria; and, after the bacterial species is grown and microcolonies appear, a sample specimen of the microcolonies is set up as described below. A 0.5 McFarland of the liquid sample or, alternatively, a sample of the grown microcolonies, is prepared as commonly known in the art and the bacteria are serially diluted, starting at about $10^5$ bacteria/ ml. To each dilution, a 1:30 dilution of HRP conjugated to an aptamer selected for a first antigenic site of *E. coli* and an antibody specific for a first antigenic site of *Salmonella*, is added to bring the final volume up to 20 ml. The 20 ml sample is added to a nitrocellulose permeable membrane which has been blocked overnight with 1% BSA blocking compounds and which has been coated with 20 ml of a 1:40 dilution of two antibodies, the first antibody specific for a second antigenic site of *E. coli* and the second antibody specific for a second antigenic site of *Salmonella*. The permeable membrane then is washed in a washing solution (PBS, pH 7.4 with 0.1% Tween 20) using a portable washing device at medium speed of rotation for about two minutes. A drop of DAB (3 mg/ml in Tris saline buffer, pH 7.6), 3% $H_2O_2$ and 1.2 weight % of $NiCl_2$ then is added to the permeable membrane. A color reaction to a grey-brown color rapidly develops in about 0.5 to 3 minutes on the surface of the permeable membrane in locations where *E. coli* and *Salmonella* are attached to the membrane via binding to their respective immobilized antibodies. *E. coli* and *Salmonella* then are detected and identified on the permeable membrane due to the color change of the *E. coli* and *Salmonella* on the permeable membrane and their respective locations on the permeable membrane, which is distinguished from the color of any other species of bacteria which may be contained in the mixture. *E. coli* and *Salmonella* are detected reliably at $10^5$ to $10^2$ bacteria/ml in as little as 30 minutes, with minimal background observed, and with no cross-reactivity to other species of bacteria. This detection and identification assay is significantly more rapid than any other microbiological diagnostic assay known to date.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A method for rapid detection and identification of one or more live target microorganisms in a sample, consisting of:
   taking a sample containing at least one live target microorganism and forming a mixture containing the at least one target live microorganism and at least one first aptamer conjugated to a reporter compound and selected for a binding site of the at least one live target microorganism and/or at least one first antibody conjugated to a reporter compound and specific for an antigenic site of the at least one live target microorganism;
   washing the mixture;
   adding the mixture to a permeable membrane, said permeable membrane having immobilized thereon at least one second aptamer selected for a binding site of the at least one first aptamer and/or at least one second antibody specific for an antigenic site of the at least one first antibody, said permeable membrane being substantially flat and two-dimensional and having a negligible volume;
   washing any non-bound microorganisms from the permeable membrane;
   adding a detection solution to the permeable membrane, said detection solution reacting with the reporter compound to cause a color reaction in the detection solution in about 3 minutes or less; and
   detecting and identifying the at least one live target microorganism based on the color reaction, wherein the method for rapid detection and identification of the at least one live microorganism takes about 30 minutes or less.

2. The method of claim 1, wherein the sample is a liquid sample.

3. The method of claim 1, wherein the at least one second aptamer is linked to an amine compound selected from the group consisting of bovine serum albumin, amine linkers and other compounds which contain an amine group, and wherein the at least one first antibody or at least one second antibody is a monoclonal or a polyclonal antibody.

4. The method of claim 1, wherein the reporter compound is selected from the group consisting of chromogenic substrates, fluorogenic substrates and enzymes; and the detection solution is selected from the group consisting of 3,3'-diaminobenzidine (DAB) or other staining solutions and alkaline phosphatase or other enzymes.

5. The method of claim 4, wherein the reporter compound is the enzyme horse-radish peroxidase and the detection solution is the staining solution 3,3'-diaminobenzidine (DAB).

6. The method of claim 1, wherein the at least one live target microorganism is selected from the group consisting of bacteria and fungi, spores.

7. The method of claim 1, wherein the permeable membrane is selected from the group consisting of nitrocellulose, regenerated cellulose, cellophane, cuprophane, dialysis membranes, nylon, polyvinylidene fluoride (PVDF) and other organic or inorganic polymer materials with naturally occurring pores or artificially created pores.

8. A method for rapid detection and identification of one or more live target microorganisms in a sample, consisting of:
   taking a sample containing at least one live target microorganism and forming a mixture containing the at least one live target microorganism and at least one first aptamer conjugated to a reporter compound and selected for a first binding site of the at least one live target microorganism and/or at least one first antibody conjugated to a reporter compound and specific for a first antigenic site of the at least one live target microorganism;
   adding the mixture to a permeable membrane having immobilized thereon at least one second aptamer selected for a second binding site of the at least one live target microorganism and/or at least one second antibody specific for a second antigenic site of the at least one live target microorganism, said permeable membrane being substantially flat and two-dimensional and having a negligible volume;
   washing any non-bound microorganisms from the permeable membrane;
   adding a detection solution to the permeable membrane, said detection solution reacting with the reporter compound to cause a color reaction in the detection solution in about 3 minutes or less; and
   detecting and identifying the at least one live target microorganism based on the color reaction, wherein the method for rapid detection and identification of the at least one live microorganism takes about 30 minutes or less.

9. The method of claim 8, wherein the sample is a liquid sample.

10. The method of claim 8, wherein the at least one second aptamer is linked to an amine compound selected from the group consisting of bovine serum albumin, amine linkers and other compounds which contain an amine group, and wherein the at least one first antibody or at least one second antibody is a monoclonal or a polyclonal antibody.

11. The method of claim 8, wherein the reporter compound is selected from the group consisting of chromogenic substrates, fluorogenic substrates and enzymes; and the detection solution is selected from the group consisting of 3,3'-diaminobenzidine (DAB) or other staining solutions and alkaline phosphatase or other enzymes.

12. The method of claim 11, wherein the reporter compound is the enzyme horse-radish peroxidase and the detection solution is the staining solution 3,3'-diaminobenzidine (DAB).

13. The method of claim 8, wherein the at least one live target microorganism is selected from the group consisting of bacteria.

14. The method of claim 8, wherein the permeable membrane is selected from the group consisting of nitrocellulose, regenerated cellulose, cellophane, cuprophane, dialysis membranes, nylon, polyvinylidene fluoride (PVDF) and other organic or inorganic polymer materials with naturally occurring pores or artificially created pores.

\* \* \* \* \*